(12) United States Patent
Beisser et al.

(10) Patent No.: US 11,724,019 B2
(45) Date of Patent: Aug. 15, 2023

(54) METHOD AND DEVICES FOR EMPTYING AN EFFLUENT BAG AFTER BLOOD TREATMENT

(71) Applicant: Fresenius Medical Care Deutschland GmbH, Bad Homburg (DE)

(72) Inventors: Nicolas Beisser, Hanau (DE);
Alexander Heide, Eppstein (DE);
Juergen Klewinghaus, Oberursel (DE);
Andreas Richter, Weilrod (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 600 days.

(21) Appl. No.: 16/631,998

(22) PCT Filed: Jul. 16, 2018

(86) PCT No.: PCT/EP2018/069283
§ 371 (c)(1),
(2) Date: Jan. 17, 2020

(87) PCT Pub. No.: WO2019/016145
PCT Pub. Date: Jan. 24, 2019

(65) Prior Publication Data
US 2020/0230301 A1    Jul. 23, 2020

(30) Foreign Application Priority Data

Jul. 18, 2017  (DE) .......................... 102017116142.2
Nov. 21, 2017  (DE) .......................... 102017127394.8

(51) Int. Cl.
*A61M 1/14* (2006.01)
*A61M 1/16* (2006.01)
(Continued)

(52) U.S. Cl.
CPC ................ *A61M 1/69* (2021.05); *A61M 1/14* (2013.01); *A61M 1/1621* (2014.02);
(Continued)

(58) Field of Classification Search
CPC ........ A61M 1/14; A61M 1/69; A61M 1/1621; A61M 1/1668; A61M 1/267; A61M 1/34;
(Continued)

(56) References Cited

U.S. PATENT DOCUMENTS 5,527,272 A    6/1996  Folden
6,485,483 B1   11/2002 Fujii
(Continued)

FOREIGN PATENT DOCUMENTS

AU    2004248985    12/2004
CA    2298135       8/2000
(Continued)

OTHER PUBLICATIONS

International Search Report and Written Opinion in Application No. PCT/EP2018/069283, dated Oct. 9, 2018, 9 pages (English Translation).

(Continued)

*Primary Examiner* — John Kim
(74) *Attorney, Agent, or Firm* — Fish & Richardson P.C.

(57) ABSTRACT

The present disclosure relates to an effluent bag for collecting accumulated blood treatment effluent. The effluent bag comprises a closeable effluent opening or connection to an exterior of the effluent bag. The disclosure further relates to methods, a blood treatment apparatus, and a discharge hose system.

24 Claims, 6 Drawing Sheets

(51) Int. Cl.
 *A61M 1/34* (2006.01)
 *A61M 60/435* (2021.01)
 *A61M 1/00* (2006.01)
 *A61M 1/26* (2006.01)
 *A61M 1/36* (2006.01)

(52) U.S. Cl.
 CPC .......... *A61M 1/1668* (2014.02); *A61M 1/267* (2014.02); *A61M 1/34* (2013.01); *A61M 1/3413* (2013.01); *A61M 1/3621* (2013.01); *A61M 1/86* (2021.05); *A61M 1/962* (2021.05); *A61M 60/435* (2021.01)

(58) Field of Classification Search
 CPC .... A61M 1/3413; A61M 1/3621; A61M 1/86; A61M 1/962; A61M 60/435
 See application file for complete search history.

(56) References Cited

U.S. PATENT DOCUMENTS

| | | |
|---|---|---|
| 8,911,390 B2 | 12/2014 | Sternby |
| 2009/0187138 A1 | 7/2009 | Lundtveit et al. |
| 2009/0299272 A1 | 12/2009 | Hopping et al. |
| 2010/0121246 A1 | 5/2010 | Peters et al. |
| 2011/0036768 A1 | 2/2011 | Ueda et al. |
| 2012/0152842 A1 | 6/2012 | Rada et al. |
| 2016/0129173 A1 | 5/2016 | Ahrens et al. |
| 2016/0222969 A1 | 8/2016 | Heide et al. |
| 2017/0014565 A1 | 1/2017 | Wiktor et al. |
| 2018/0228961 A1 | 8/2018 | Takeuchi et al. |

FOREIGN PATENT DOCUMENTS

| | | |
|---|---|---|
| CN | 1761494 | 4/2006 |
| CN | 201320318 | 10/2009 |
| CN | 202146469 | 2/2012 |
| CN | 205031625 | 2/2016 |
| CN | 105582582 | 5/2016 |
| CN | 106061524 | 10/2016 |
| DE | 10011208 | 9/2001 |
| DE | 102006012087 | 9/2007 |
| DE | 102017122804 | 4/2019 |
| EP | 1398018 | 3/2004 |
| EP | 2156855 | 2/2010 |
| EP | 2465555 | 6/2012 |
| EP | 2616117 | 7/2013 |
| JP | H04-090310 | 8/1992 |
| JP | H04-131243 | 12/1992 |
| JP | H07-024062 | 1/1995 |
| JP | H09-322936 | 12/1997 |
| JP | H10-234849 | 9/1998 |
| JP | 2017-500903 | 1/2017 |
| JP | 2017-080147 | 5/2017 |
| WO | WO 2000/002617 | 1/2000 |
| WO | WO 2008/120803 | 10/2008 |
| WO | WO 2012/035040 | 3/2012 |
| WO | WO 2015/058841 | 4/2015 |
| WO | WO 2015/098709 | 7/2015 |

OTHER PUBLICATIONS

International Preliminary Report on Patentability in Application No. PCT/EP2018/069283, dated Jan. 21, 2020, 7 pages.

METHOD AND DEVICES FOR EMPTYING AN EFFLUENT BAG AFTER BLOOD TREATMENT

CROSS-REFERENCE TO RELATED APPLICATIONS

The present application is the national stage entry of International Patent Application No. PCT/EP2018/069283, filed on Jul. 16, 2018, and claims priority to Application No. DE 102017116142.2, filed in the Federal Republic of Germany on Jul. 18, 2017, and DE 102017127394.8, filed in the Federal Republic of Germany on Nov. 21, 2017, the disclosures of which are expressly incorporated herein in its entirety by reference thereto.

TECHNICAL FIELD

The present disclosure relates to an effluent bag, methods for emptying an effluent bag, a blood treatment apparatus, and a discharge hose system.

BACKGROUND

Extracorporeal blood treatment is known from practice. Thereby, the patient's blood is taken and fed along an extracorporeal blood circuit and, for example, through a blood filter. The blood filter comprises a blood chamber through which blood is led, and a dialysis liquid chamber, through which dialysis liquid is led. Both chambers are separated from each other by a semi-permeable membrane. Blood and dialysis liquid are mostly guided by the counter current principle through the blood filter. The blood is cleaned in the blood filter. On exiting the blood filter, the dialysis liquid, from now on referred to as dialysate, is regarded as used and is discarded. In addition to the dialysate, the fluid to be discarded also comprises filtrate, which comprises water which has been withdrawn from the blood in the blood filter. Filtrate and dialysate will be referred to individually or collectively in the following simply as effluent.

SUMMARY

The effluent is, in practice, fed to an effluent bag via an effluent inlet line and is first stored in the effluent bag. After completion of the blood treatment, or in bag emptying intervals during the blood treatment (intervals in which the bag is emptied), the effluent is disposed of from the effluent bag into a sink or a basin over which it is held.

An effluent bag is described herein. Further, specified is a method to empty the effluent bag, a discharge hose system and a blood treatment apparatus, with which the method is executable.

The present disclosure relates to an effluent bag, which is designed to collect accumulated effluent during a blood treatment. The effluent bag comprises at least one or specifically one, optionally closeable, effluent opening or connection to an exterior of the effluent bag.

In a method for emptying an effluent bag an effluent bag is described.

Furthermore, a switching device is operated so that a fluid connection can be established between the interior of the effluent bag and the interior of the effluent outlet line, which is connected to the switching device. Additionally or alternatively to this step, the effluent inlet line is detached from the blood treatment apparatus and its unattached end positioned in proximity to the basin in order to empty the effluent bag. Clamps, where provided, may be closed in order to prevent an unwanted leakage of effluent from the blood treatment apparatus while the effluent outlet line for emptying the effluent bag is detached from the blood treatment apparatus.

A method for emptying an effluent bag comprises providing an effluent bag with both an inlet for effluent and an outlet for effluent.

The inlet of the effluent bag is thereby detachable from or releasably connected to an effluent inlet line via a connector.

The outlet is connected to an effluent outlet line. A pump is provided along the effluent outlet line. The effluent outlet line is arranged to feed effluent into a basin.

The method further comprises separating the effluent inlet line from the inlet using the connector; the connector may be opened for this purpose. The connection between the effluent inlet line and the effluent bag is thereby interrupted. Additionally or alternatively, a pump, which is arranged along the effluent inlet line for pumping the effluent, is stopped. The blood treatment apparatus described herein is connected to a dialysate outlet line, which may correspond to the line referred to herein as the effluent inlet line and which feeds effluent to an effluent bag. It is connected via this line to an effluent bag.

The discharge hose system described herein comprises an effluent inlet line, which is connected to the switching device. The discharge hose system further comprises an effluent outlet line which is connected to the switching device. Thereby, the switching device optionally comprises a connector or a hose section, which may provide a fluid connection between an effluent bag and the switching device. Thereby, the switching device enables either a fluid connection between the connector or the effluent bag and the effluent inlet line or between the connector or the effluent bag and the effluent outlet line.

Embodiments described herein may comprise some, each or all of the following features in any arbitrary combination, as far as this is technically possible for the person skilled in the art. Advantageous developments are also subject-matter of the dependent claims.

In all of the following embodiments, the use of the expression "may be" or "may have" and so on, is to be understood synonymously with "preferably is" or "preferably has" and so on respectively, and is intended to illustrate embodiments.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" always as "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Whenever an embodiment is mentioned herein, it is then an exemplary embodiment according to the present disclosure.

The discharge hose system described herein may be understood optionally as a kit or set (or as a part thereof), which in some embodiments comprises further components (such as a charging station), which are not in contact with the conveyed fluid in order to convey it.

In some embodiments, the effluent bag comprises specifically one effluent opening, which serves both as an effluent inlet opening and as an effluent outlet opening. It may be the only liquid opening of the effluent bag, it may be the single only opening of the effluent bag. In several embodiments the effluent bag additionally comprises a vent opening.

In several embodiments, the effluent bag is connected to only one hose section, connector, or to only one line.

In several embodiments, the effluent opening is closeable and/or provided with a cover.

In several embodiments, the effluent bag may be a container of any kind, for example a container having a flexible outer skin such as a film, or being of film, a container having or being a hard outer shell, such as a canister, etc.

In several embodiments, the effluent bag is connected to, or arranged to be connectable to a discharge hose system, or is a part thereof. The discharge hose system, or parts thereof, comprise at least or only one line, namely an effluent inlet line leading to the effluent bag.

The effluent inlet line may be used in an embodiment of the method, either in order to be connected to the blood treatment apparatus in which case it serves to fill the effluent bag, or in order to be positioned near the basin, in which case it serves to empty the effluent bag. Clamps may be provided in order to prevent an unwanted leakage of effluent from the blood treatment apparatus while the effluent outlet line is detached from the blood treatment apparatus, in order to empty the effluent bag. This embodiment is distinctive for its simplified and economical construction. A power supply etc. is, advantageously, not necessary with this design. Consequently, risks to the patient are not expected due to the absence of a power supply.

Suitable, optional hose connectors or connector pairs may simplify releasing the effluent inlet line from the blood treatment apparatus. Suitable, optional brackets may facilitate keeping, at least, the free end of the effluent inlet line near the basin.

Optionally, the effluent bag or the discharge hose system further comprises an effluent outlet line leading away from the effluent bag and a, preferably electrically insulating, switching device, via which a fluid connection may be achieved. This fluid connection is achieved via the switching device, either between the interior of the effluent bag and the effluent inlet line ("first position"), or between the effluent bag and the effluent outlet line ("second position"), these connections are mutually exclusive.

It may be determined in a high-voltage test that the switching device is electrically insulating.

For example, with the help of a high-voltage tester it may be determined whether the switching device provided on the effluent bag insulates the interior of the effluent bag against a test voltage of 1500 volts AC. For this purpose, the effluent bag may be filled with a sodium chloride solution (e.g. 0.9%, short: NaCl-solution). A first electrode for the test voltage is in contact with the NaCl-solution, a second electrode is in contact with the switching device outlet. The switching device is, for example, opened and closed 10 times, so that the interior of the switching device and the interior of the hose is filled with NaCl. The second electrode, for example, is subjected to a voltage of 1500 volts AC (10 sec increase, 60 sec holding, 10 sec decrease). This process may be repeated several times. Subsequently, the switching device is opened and a control test is carried out. The switching device may be considered sufficiently insulating, if there is no voltage breakdown or rather no inadmissible current flow detected during the high-voltage test.

In some embodiments, the switching device comprises or is a three-way-tap (alternatively referred to as a three-way-valve).

In certain embodiments the switching device consists of glass or plastic or comprises at least one of these materials.

In some embodiments, the switching device can be switched between exactly two positions, namely, only between the first and the second position.

In several exemplary embodiments, the switching device is a multi-way-tap or -valve having more than three paths or connections.

In certain embodiments, the effluent outlet line is in conveying connection with at least a pump or a pump drive.

In some embodiments, this pump or this pump drive comprises at least a magnetically mounted or driven pump section, in particular a pump head. This pump section or pump head is, for example, designed as an impeller pump head or as its rotor. This type of mounting or driving serves to protect the patient from an electric shock.

In several embodiments, the pump drive, particularly of a blood treatment apparatus or of a pump not forming part of the blood treatment apparatus, is manually connected to the pump head of the discharge hose system.

In some embodiments, the operation of the pump drive is manually started and/or stopped.

In certain embodiments, the switching device is operated in such a way that a fluid connection, which exists between the interior of the effluent bag and the interior of the effluent outlet line, may be interrupted.

In some embodiments, the blood treatment apparatus comprises a control device, which is configured to carry out the method. In other embodiments this is not the case.

In certain embodiments, the blood treatment apparatus is designed as a hemodialysis apparatus, hemofiltration apparatus or hemodiafiltration apparatus, in particular as an apparatus for chronic renal replacement therapy or continuous renal replacement therapy (CRRT).

In several embodiments, the blood treatment apparatus comprises a charging station for a voltage source for the pump drive of the pump. The voltage source may be a low voltage- or low current source.

In some embodiments, the discharge hose system further comprises an effluent bag.

In several embodiments, the discharge hose system comprises the charging station for a voltage source for the pump drive of the pump, for example for a rechargeable battery.

In several embodiments, the discharge hose system comprises at least a check valve or non-return valve, e.g. downstream of the optional pump. The non-return valve may advantageously prevent an unwanted leakage of effluent from the effluent outlet line, which improves cleanliness and hygiene.

In several embodiments, the discharge hose system comprises at least a connector pair. Connector pairs are optional. They can advantageously serve to facilitate the assembly of the discharge hose system used out of known components.

In several embodiments, the discharge hose system comprises a control or closed loop control device or is in signal connection herewith, which is configured or programmed to switch the switching device in such a way that the effluent bag is, optionally via the connection line, sometimes connected to the effluent inlet line ("first position") and is sometimes connected to the effluent outlet line ("second position") in fluid communication. This control or closed loop control device is preferably not a control or closed loop control device of the blood treatment apparatus.

In several embodiments, a control or closed loop control device of the blood treatment apparatus is not configured or programmed to switch the switching device in such a way that the effluent bag is sometimes connected to the effluent inlet line and sometimes connected to the effluent outlet line.

The control or closed-loop control device of the blood treatment apparatus and/or the control or closed-loop control device of the discharge hose system may be programmed in such a way so that both the switching via switching device, that sometimes connects the effluent bag to the effluent inlet line and sometimes connects it to the effluent outlet line, and the starting and/or stopping of the pump connected to the effluent outlet line, are coupled together, or are automatically performed together, consecutively, dependently of each other, etc.

Thereby, for example, the pump may start automatically, whenever the effluent outlet line is connected or is being connected to the effluent bag (second position), by switching—manually or automatically—between the positions on the switching device. Additionally or alternatively for example, the pump may automatically stop, whenever the effluent inlet line is connected or is being connected—manually or automatically—to the effluent bag (first position). Sensors, devices etc. which are necessary for this may be provided.

In some embodiments, the blood treatment apparatus comprises a control or closed-loop control device. The control or closed-loop control device may be programmed and/or configured to carry out the method in interaction with other devices, in particular with a blood treatment apparatus.

The discharge hose system may be disposable.

In some embodiments, the switching device acts as electrically insulating. This may preferably be understood as, that fluids, which may enter into the switching device via a connector or connection point of the switching device, such as the three-way-tap (for example, the effluent influx into the effluent bag), and those surfaces which said fluids then come into contact with may not come into contact with other fluids, which can enter into the switching device via another connector or connection point of the switching device (for example, the effluent out-flux out of the effluent bag), and those surfaces, which said fluids then come into contact with, may not come into contact with each other in order to avoid conducting electricity, and/or they are non-conducting.

In some embodiments, the effluent bag, in order to be emptied or for at least one emptying process, is not removed or taken away from its position, the weighing device and/or the blood treatment apparatus.

The method may include, that after the effluent bag is partially or fully emptied, the effluent inlet line is again connected to the blood treatment apparatus, and/or via the switching device a fluid connection is again achieved between the effluent inlet line and the effluent bag, which corresponds to a return from the second position to the first position of the switching device.

In some embodiments, the effluent is removed from the effluent bag without the use of a pump, in other embodiments this is achieved by using at least one pump.

In several embodiments, the method comprises closing a shut-off element arranged in the effluent outlet line. This serves to shut off the fluid flow via the shut-off element.

In some embodiments, the shut-off element will only then be opened if the pump for the effluent, which is arranged in the effluent inlet line, has been stopped.

In several embodiments, the discharge hose system or the discharge hose system used, which is arranged downstream of the effluent bag, does not comprise a flow-divider.

The discharge hose system may, however, comprise a roller pump, such as a pump arranged in the effluent outlet line. This roller pump may optionally be connected to specifically one supply line and to specifically one discharge line. So that, the pump clearly cannot divide the incoming flow into several flows.

In several embodiments, the discharge hose system, which is arranged downstream of the effluent bag and/or downstream of the pump of the effluent outlet line, does not comprise a connector.

In several embodiments, the discharge hose system, which is arranged downstream of the effluent bag, does not comprise an element, upstream and/or downstream of pump for the effluent outlet line, that would be connected to an electrical control device, such as an electrically connected connector. This optionally does not apply to the pump; it may be electrically connected. It is also optional that it is not electrically connected, for example, to a control device.

In several embodiments, the switching device is connected directly or indirectly to the—optional only—effluent opening of the effluent bag. If the switching device is indirectly connected to the—optional only—effluent opening of the effluent bag, this fluid connection may be established via the connection line disclosed herein, preferably only via this line. Thereby, the position of the switching device may be responsible for the direction of flow of the fluid either only into the effluent bag or only out of the effluent bag, for example through the switching device.

The connection line may be the only fluid line into or out of the effluent bag.

The connection line may be connected exclusively to the switching device and the effluent bag, i.e. not also being in fluid communication with further lines, containers etc.

In several embodiments, the connection line is not in fluid communication with a cassette, for example a disposable cassette, or a port thereof.

In several embodiments, the switching device is, in each case directly or indirectly, connected exclusively to the—optional only—effluent opening of the effluent bag, the effluent inlet line as well as to the effluent outlet line in order to control or convey fluids.

In several embodiments, the switching device is operated in such a way that a fluid communication is established between the interior of the effluent bag and the interior of the effluent outlet line, connected to the switching device. Additionally, a fluid exchange between the effluent inlet line and the effluent bag is prevented by the switching device, e.g. simultaneously and/or forcibly guided.

In several embodiments, the switching device is not a clamp, not a two-way valve or not a valve that may vary the flow through a line or along only one line, e.g. a hose, in only one flow direction.

In several embodiments, the devices and apparatuses, in particular the blood treatment apparatus and/or the discharge hose system, comprise only one effluent bag, but not two or more effluent bags.

In several embodiments, the methods only relate to one effluent bag, but not to two or more effluent bags.

In several embodiments, the filling or emptying of the effluent bag is not brought about by or does not take place because of the controlling or regulating of a control device or a closed-loop control device.

Some or all embodiments may comprise one, several or all of the advantages mentioned above and/or in the following.

All of the advantages achievable with the methods described herein can also be achieved undiminished in certain embodiments of the devices described herein.

An advantage of the present disclosure is that the effluent bag, as is the case with conventional collection bags, does not need to be manually removed from the machine to be emptied over, for example, a basin, which, in view of an effluent bag of up to 10 kg, presents an unpopular and physically demanding task. Rather, it may remain on the treatment machine's weighing device to be emptied.

The effluent bag and method of emptying the effluent bag advantageously avoids the risk of an electrically conductive contact occurring from the liquid to the ground when emptying the contents of the effluent bag, otherwise the permissible patient leakage current would be exceeded.

An advantage achievable with certain embodiments is that both actions, namely both the filling and emptying of the effluent bag, through the integration of the operating components for this purpose being coupled together into one component, are connected to each other for joint operation. The forced coupling helps to ensure that manual steps relating to emptying are not forgotten. Moreover, manual or automatic steps are saved. The flow paths between basin or drain and dialyzer or patient may preferably be electrically separated from each other, which acts in the interest of the patient's safety.

Furthermore it is advantageous that the switching device may be provided to be manually operated. Therefore, many embodiments do not require an intervention in the control or regulation of the blood treatment apparatus and, therefore, also advantageously allow a cost-effective retrofit of existing systems.

A further advantage lies in the ease of construction required to implement the effluent bag and blood treatment apparatus with the effluent bag.

BRIEF DESCRIPTION OF THE DRAWINGS

In the following, the present invention is described with reference to the accompanying figures which are purely exemplary. In the figures same references numerals designate same or like components, wherein.

DETAILED DESCRIPTION OF THE DRAWINGS

Figure 1:
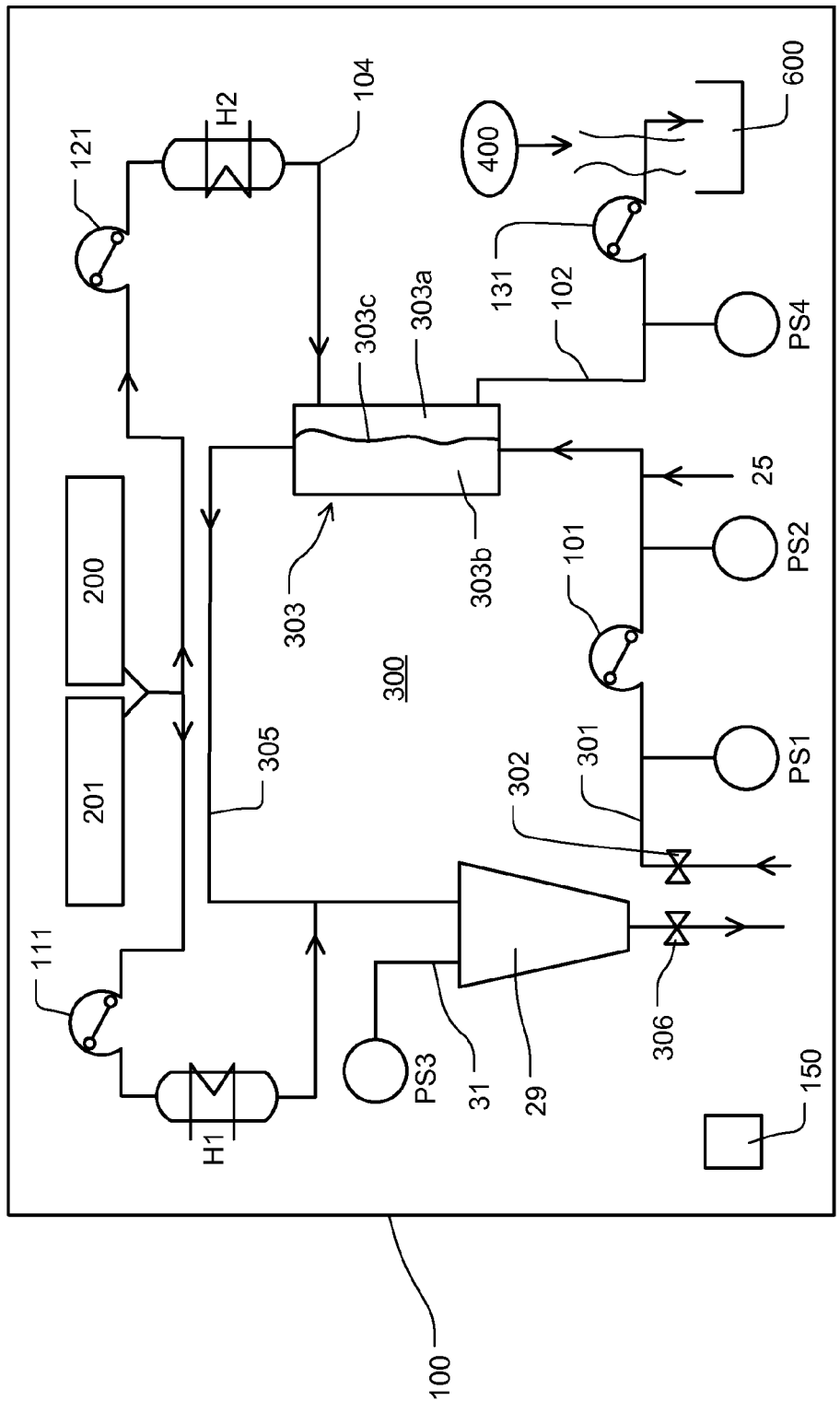
FIG. 1 shows in a simplified representation a blood treatment apparatus comprising an extracorporeal blood circuit in a first embodiment.

FIG. 1 shows in a greatly simplified representation a blood treatment apparatus 100 according to the present disclosure connected to an extracorporeal blood circuit 300 and an only indicated discharge hose system having an effluent bag 400. Discharge hose system and effluent bag 400 are set out in the figures below.

The extracorporeal blood circuit 300 comprises a first line 301 in the form of an arterial line section.

The first line 301 is in fluid communication with a blood treatment apparatus, here an exemplary blood filter or dialyzer 303. The blood filter 303 comprises a dialysis fluid chamber 303*a* and a blood chamber 303*b*, which are separated from each other by a mostly semi-permeable membrane 303*c*.

The extracorporeal blood circuit 300 further comprises at least a second line 305 in the form of a venous line section. Both the first line 301, as well as the second line 305, can serve for their connection to the patient's vascular system (not shown).

The first line 301 is optionally connected with a (first) hose clamp 302 for blocking or closing line 301. The second line 305 is optionally connected with a (second) hose clamp 306 for blocking or closing line 305.

The blood treatment apparatus 100 (which is represented only by some of its devices and merely schematically in FIG. 1) comprises a blood pump 101. During the patient's treatment the blood pump 101 conveys blood through sections of the extracorporeal blood circuit 300 towards the blood filter or dialyzer 303. This is indicated by the small arrow-tips, which are used in each of the figures to generally illustrate the direction of flow.

Fresh dialysis liquid is pumped from a source 200 along the dialysis liquid input line 104 into the dialysis liquid chamber 303*a*, by a pump for dialysis liquid, which may be designed as a roller pump or as an otherwise occluding pump. The dialysis liquid leaves the dialysis liquid chamber 303*a* in the direction of the basin 600, as dialysate possibly enriched by filtrate, and is herein referred to as effluent.

The source 200 may be, for example a bag or a container. The source 200 may also be a fluid line through which the online and/or continuously generated or mixed liquid is provided, for example a hydraulic output or connection of the blood treatment apparatus 100.

A further source 201 with substitute may be optionally provided. It may be identical, or correspond to the source 200, or be a separate source.

An only indicated control or closed-loop control device 150 can be configured to carry out the aforementioned method. Optionally it may be carried out manually.

At the bottom right of FIG. 1 is indicated where the discharge hose system with the effluent bag 400 is connected to the blood treatment apparatus 100. Discharge hose system, effluent bag 400 and connection are only shown in the following figures.

In addition to the aforementioned blood pump 101, the arrangement in FIG. 1 further comprises purely optionally a series of further pumps, in each case optional, namely the pump 111 for substitute, the pump 121 for dialysis liquid, and the pump 131 for the effluent.

The pump 121 is provided to supply dialysis liquid from a source 200, for example a bag, via an optionally existing bag heater with a bag H2 to the blood filter 303, via a dialysate liquid inlet line 104.

The supplied dialysis liquid exits from the blood filter 303 via a dialysate outlet line 102, supported by the pump 131, and may be discarded.

Upstream of blood pump 101 an optional arterial sensor PS1 is provided. During the patient's treatment it measures the pressure in the arterial line.

Downstream of the blood pump 101, but upstream of the blood filter 303 and if provided, upstream of a coupling site 25 for heparin, a further optional pressure sensor PS2 is provided. It measures the pressure upstream of the blood filter 303 ("pre-hemofilter").

Again, a further pressure sensor may be provided as PS4 downstream of the blood filter 303, however preferably upstream of the pump 131 in the dialysate outlet line 102, in order to measure the filtrate pressure of the blood filter 303.

Blood, which leaves the blood filter 303, passes through an optional venous blood chamber 29, which comprises a ventilation device 31 and can be in fluid communication with a further pressure sensor PS3.

The exemplary arrangement shown in FIG. 1 comprises a control or closed-loop control device 150. It may be in cable or wireless signal connection to any of the components referred to herein—in particular or at least to the blood pump 101—in order to control or regulate the blood treatment apparatus 100. It is optionally configured to carry out the herein described method.

The optional pump 111 is provided to supply substitute from the optional source 201, for example a bag, via an optionally existing bag heater H1 with a bag, to the second line 305.

Figure 2:
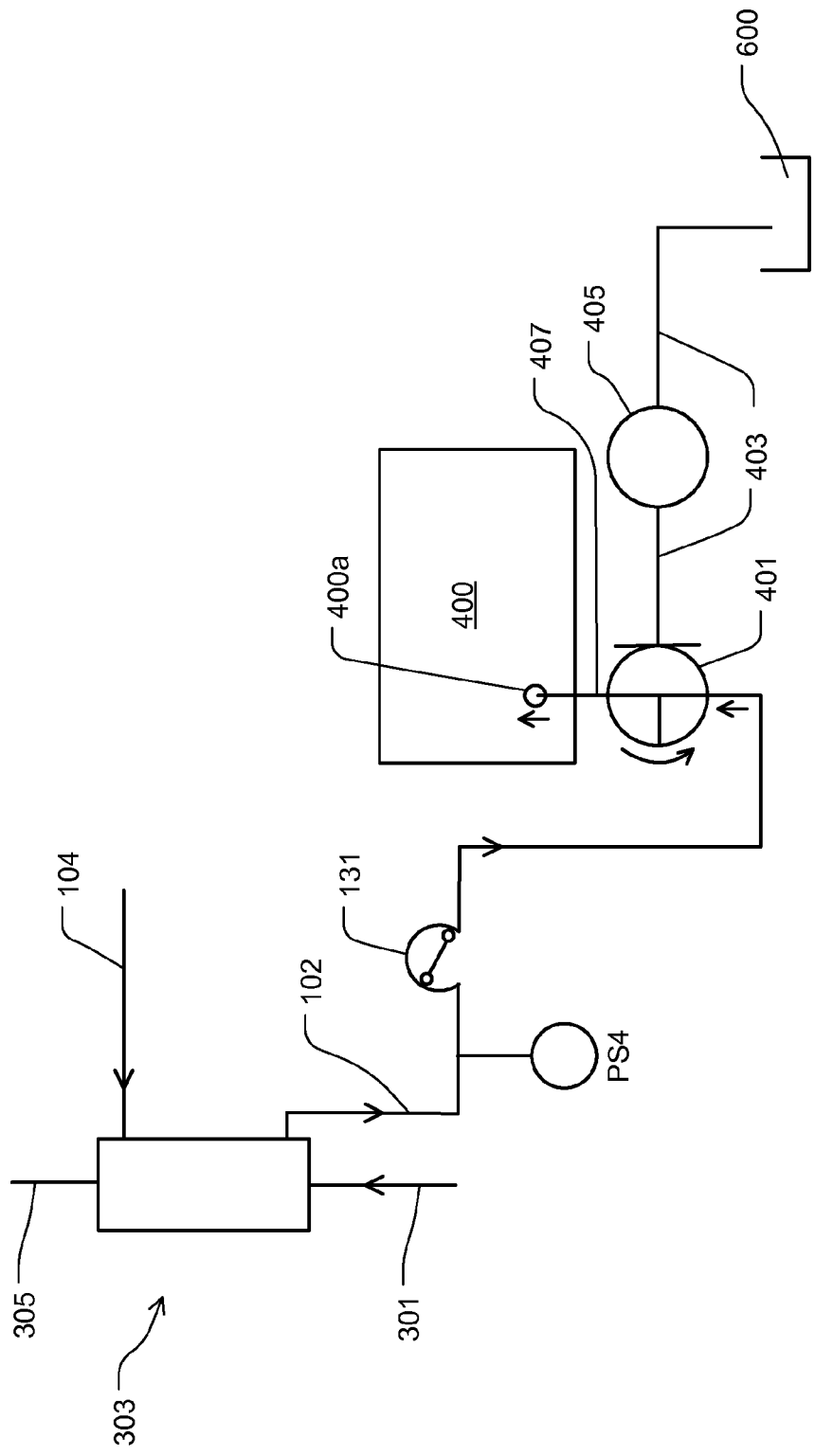
FIG. 2 shows in a simplified representation, a discharge hose system having an effluent bag, whereby effluent is fed into the effluent bag from the effluent inlet line.

FIG. 2 shows in a simplified representation a discharge hose system having an effluent bag 400 at the moment during which the effluent is fed to the effluent bag 400.

A switching device 401, here exemplarily embodied as a three-way-tap 401, is arranged on the dialysate outlet line 102 between the pump 131 for the effluent and the effluent bag 400, but in any case upstream to the effluent bag 400. Dialysate (and/or effluent) from the blood filter 303 drains out via the dialysate outlet line 102. It also serves as an effluent inlet line, which feeds the effluent to the effluent bag 400.

As shown in FIG. 2, the three-way-tap 401, in its position shown in FIG. 2, fluidly connects the dialysate outlet line 102 with the effluent inlet opening (which is also the effluent outlet opening, therefore, in short: effluent opening) 400a of the effluent bag 400.

In this first position, the effluent outlet line 403, which is also connected to the three-way-tap 401, is blocked. The effluent outlet line 403 is in turn, directly or indirectly, connected to the basin 600.

In the first position shown in FIG. 2, effluent may get to the effluent bag 400 from the dialysate outlet line 102 via the three-way-tap 401, but not to the effluent outlet line 403. The three-way-tap 401, due to its design, may be made from electrically insulating material and/or in the places in which it is fluid conveying effect an electrical insulation.

The effluent outlet line 403 may comprise a pump 405 and lead into the basin 600.

The pump 405 is arranged downstream of the effluent bag 400 but upstream of the basin 600.

Figure 4:
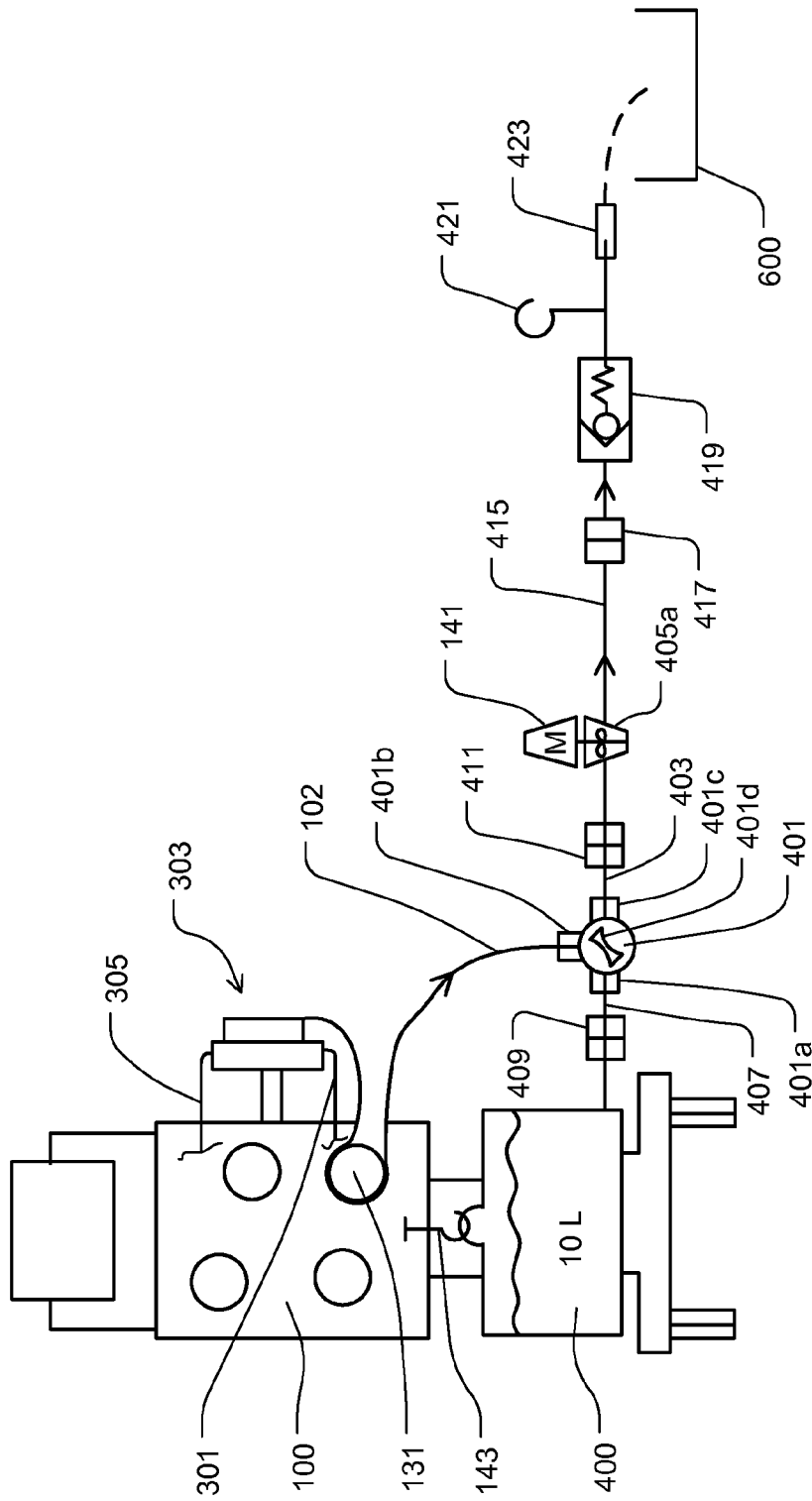
FIG. 4 shows a further embodiment of the blood treatment apparatus having a discharge hose system and an effluent bag.

The pump 405, as first shown in FIG. 4, may optionally comprise or have at least one pump drive 141 and a pump head 405a (not shown in FIG. 2). It is not in operation ("OFF") in its position as shown in FIG. 2, as there is no effluent present in the effluent outlet line 403 which could be discarded via the pump 405 into the basin 600.

In each embodiment, the pump 405 may be a roller pump. Alternatively, in any embodiment, it is not a roller pump.

Figure 3:
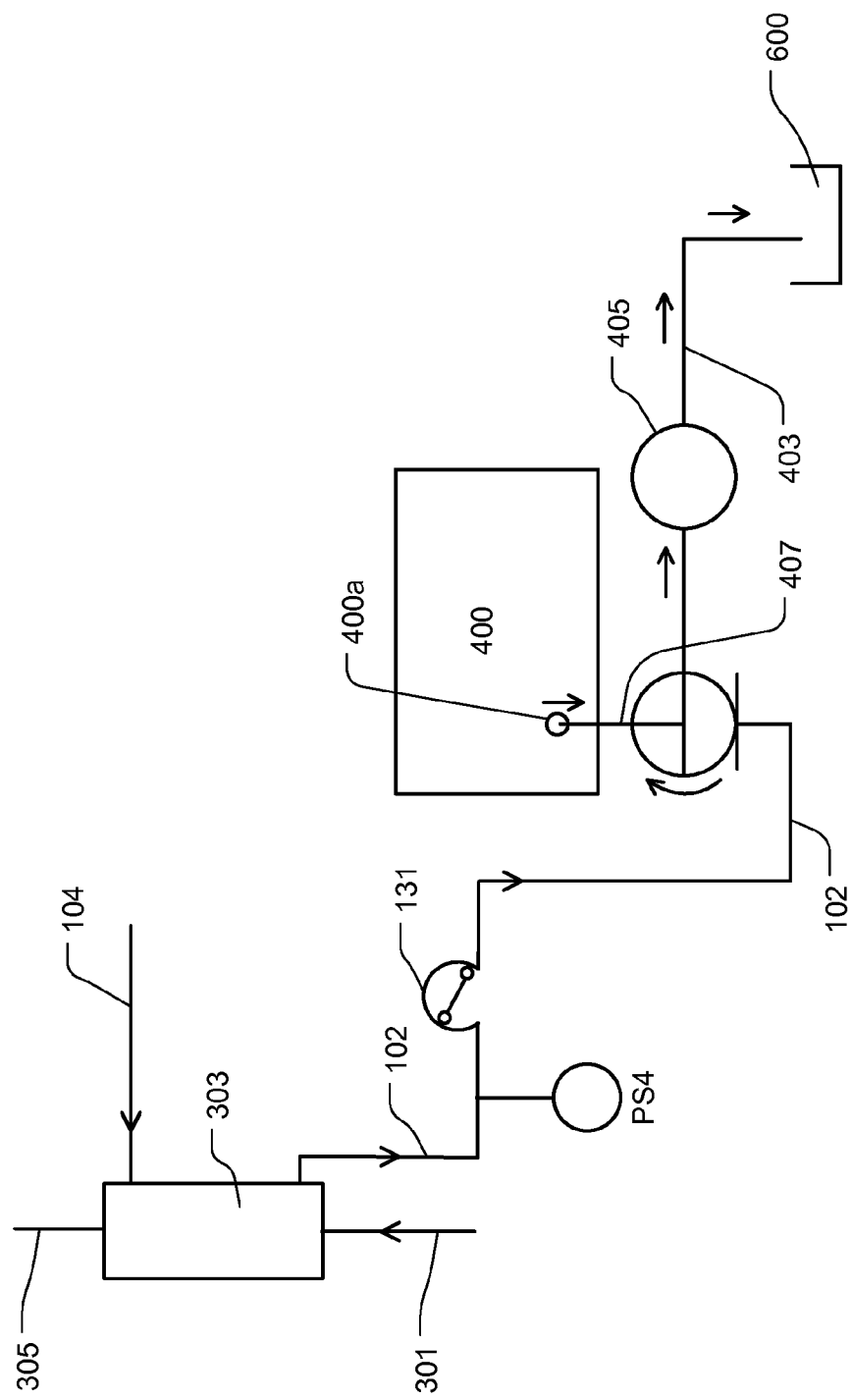
FIG. 3 shows in a simplified representation, a discharge hose system having an effluent bag, whereby effluent is fed from the effluent bag into the effluent outlet line.

FIG. 3 shows a simplified representation of a discharge hose system having an effluent bag 400, while effluent is led away from the effluent bag 400.

The three-way-tap 401 in its position shown in FIG. 3 does not fluidly connect the dialysate outlet line 102 with the effluent opening 400a of the effluent bag 400.

In this second position the effluent outlet line 403, which is connected also to the three-way-tap 401 and in turn to the basin 600, is disconnected from the dialysate outlet line 102.

In the second position shown in FIG. 3 the effluent from the dialysate outlet line 102 cannot pass through the three-way-tap 401 to reach the basin 600, nor to reach the effluent bag 400. The flow paths are thereby preferably electrically insulated.

The pump 405 is in mode ("ON") and conveys effluent out of the effluent bag 400 into the basin 600.

FIG. 4 shows the blood treatment apparatus 100 having an optional disposable discharge hose system and an effluent bag 400 having additional optional components of the discharge hose system.

These additional optional components include the connectors 401a, 401b and 401c by which the three-way-tap 401 is connected to a connection line 407 as a first hose section, to the dialysate outlet line 102 as a second hose section and/or the effluent outlet line 403 as a third hose section.

The first hose section is optional. The three-way-tap 401 may, alternatively, be connected directly to the effluent opening 400a.

The third hose section is, as effluent outlet line 403, connected to the suction side of a pump head 405a of pump 405. The pump head 405a may be part of the effluent outlet line 403, which may in turn be disposable. The pump head 405a may be magnetically mounted, which may simplify connecting the pump head 405a to other sections of the pump 405 and advantageously help to avoid a transmission of electricity or current between the connected components.

The pressure side of the pump head 405a is connected to a line 415, which may be considered an extension of the effluent outlet line 403 or as a fourth hose section.

Preferably downstream of the pump-head 405a, the effluent outlet line 403 or the line 415 comprises a fixing element or fastening device 421, by which the line or the discharge hose system, collectively, can be detachably fastened above a basin 600. The fastening device 421 may be or comprise a hook or a suction pad etc.

The line 415 or the discharge hose system may be fastened, for example, to a sink edge, a basin or the like, by the fastening device 421.

An optional end piece 423 of the line 415 or the discharge hose system may be designed, to allow for example, a splash free flow or very even flow into the basin 600, e.g. the clinic sewer, the sink, the sewer system and so forth. It may optionally comprise a corresponding connector, attachment or a thread etc.

The three-way-tap 401 comprises an optional grip section 401d, by which it may at least be moveable between its positions discussed in FIGS. 2 and 3. The hereto carried out movements are indicated by curved arrows in the FIGS. 2 and 3.

Connectors 409, 411 and/or 417 are optionally provided. The same applies to an optional check valve or non-return valve 419, preferably provided downstream of the pump 405.

The pump drive 141 of the pump 405 may be a part of the treatment apparatus. Optionally, it is, however, part of a, for example mobile, device. The latter preferably has no electrical and/or physical contact with the treatment apparatus. Preferably, the device will be powered from a, preferably chargeable, voltage source which, during the operation of the pump, is not connected to the electrical system of the treatment apparatus and/or of the clinic.

The effluent bag 400 is connected to a weighing device in order to weigh its weight or the weight of the fluid collected in it or to determine a weight change. For example, the effluent bag 400 may lie as a collection bag on a weighing surface of the weighing device or hang on a weighing hook 143.

Figure 5:
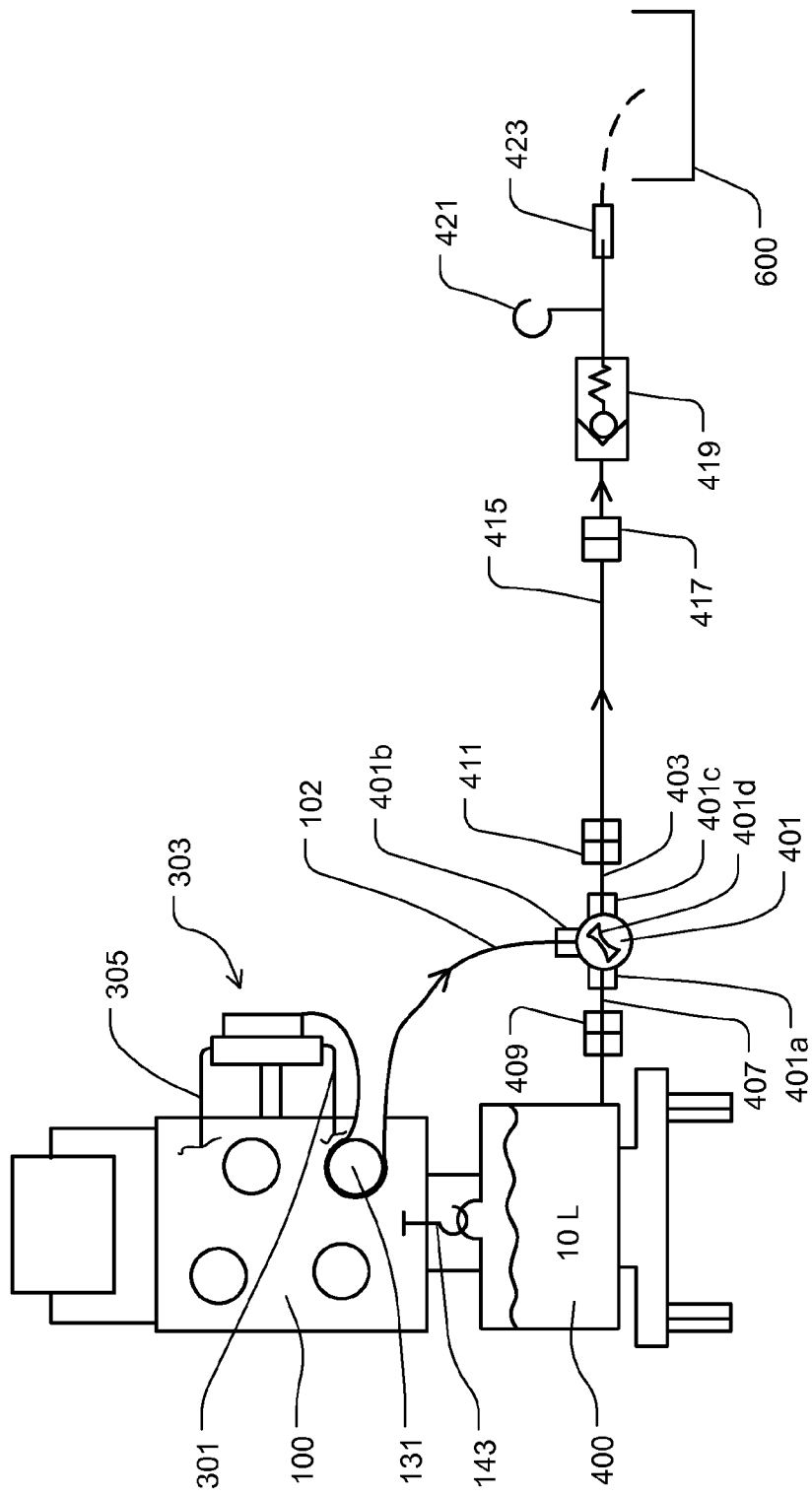
FIG. 5 shows again a further embodiment of the blood treatment apparatus encompassing a further discharge hose system and an effluent bag.

FIG. 5 shows a further embodiment of the blood treatment apparatus 100 having a further discharge hose system and an effluent bag 400, based on the embodiments in FIG. 4.

As can be seen in FIG. 5, the discharge hose system does not comprise a pump 405 (see FIG. 4). The effluent empties itself in the second position of the three-way-tap 401 without the support of a pump, e.g. through gravity alone.

The non-return valve 419 is adapted to the pressure conditions prevalent in this embodiment. Alternatively, no non-return valve 419 is provided in any embodiment.

Figure 6:
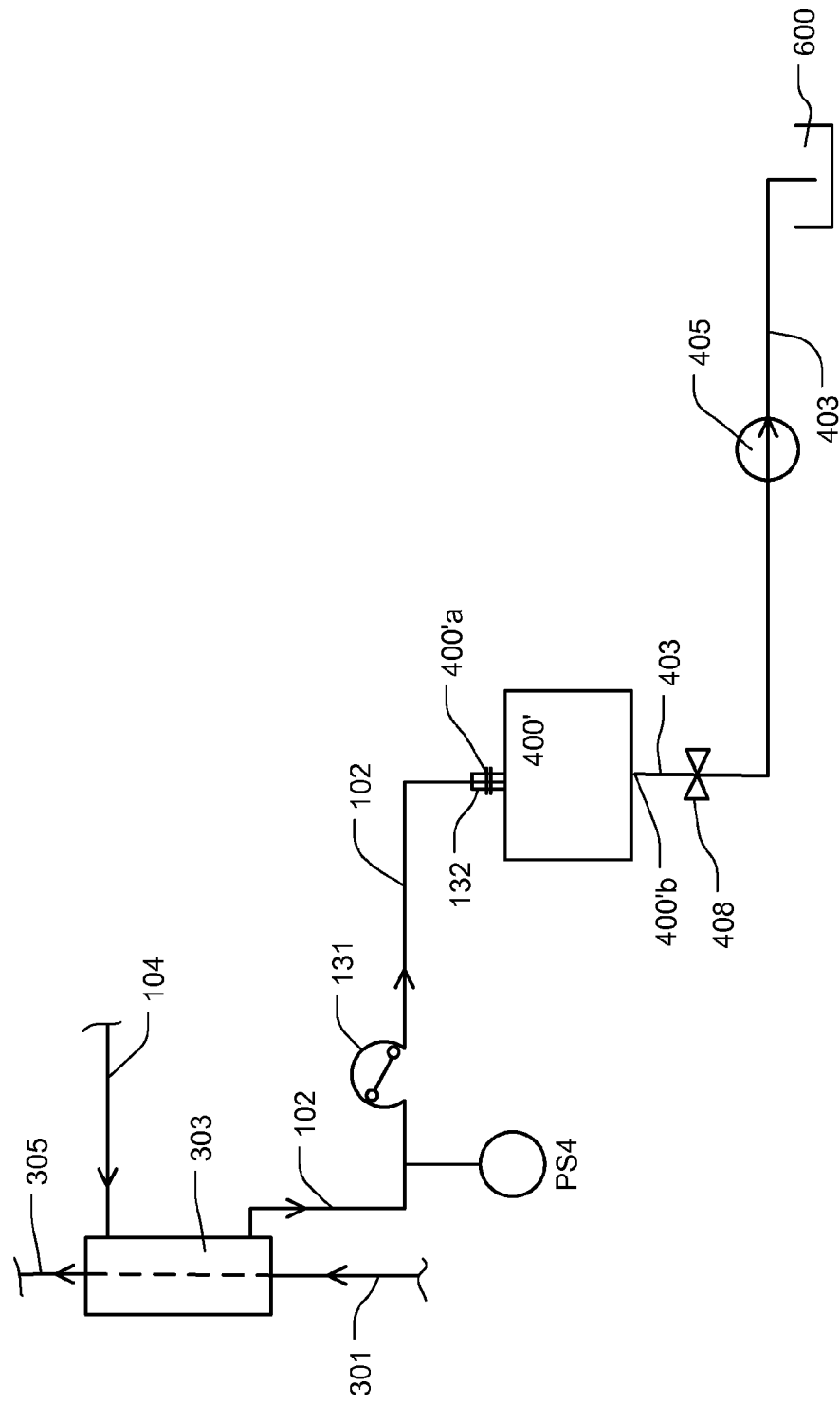
FIG. 6 shows a use of a conventional effluent bag with a discharge hose system.

FIG. 6 shows a use of a conventional effluent bag 400' with a discharge hose system, while the effluent bag 400' is fed with effluent.

During a conventional bag changing interval of the blood treatment apparatus, in particular the apparatus being from the group: dialysis machine, hemodiafiltration machine, hemofiltration machine, the conventional effluent bag 400' is carried manually to a basin 600 and emptied over it.

The conventional effluent bag, shown in FIG. 6 with the reference number 400', comprises two effluent openings; namely, on the one side, the known effluent inlet opening 400'a, with a connection to the effluent inlet line 102, and the known effluent outlet opening 400'b, with a, in particular manual, optional stopcock resp. stop-valve 408, arranged in the effluent outlet line 403, on the other.

In order to empty the effluent bag 400' the pump 131 for the effluent is stopped during the bag changing interval. Thereby, the liquid-filled section of the effluent inlet line 102, running upstream of the pump 131, is electrically isolated from the section of the liquid-filled effluent inlet line 102, running downstream of the pump 131. Thereby, the permissible limits of the patient leakage current are not exceeded. The stationary, occluding pump 131 (roller pump) thus isolates the columns of liquid upstream of pump 131 resp. downstream of pump 131 from each other. The prevailing gravity may contribute to this, in that the column of liquid present downstream of pump 131, is broken into droplets and is gravitationally pulled towards the effluent bag 400' or moves in its direction.

In order to fall further below the permissible limits of the patient leakage current, the effluent inlet line 102 may, alternatively or additionally, be separated from the effluent bag 400'. This may be done using an optionally provided connector 132, which connects the section of the liquid filled effluent inlet line 102 running downstream of the pump 131, to the effluent bag 400', or with another device.

The effluent inlet line 102 may optionally be closed with a cap after its disconnection and/or closed using a manual hose clamp downstream of the pump 131 (cap and hose clamp are not shown in FIG. 6).

The optional opening of the connector 132 means no extra effort in comparison to the aforementioned conventional, manual emptying over a basin 600, because thereby the effluent inlet line 102 must also be disconnected from the effluent bag 400'.

Only after the pump 131 for the effluent is stationary or stopped, the shut-off element 408, that may be e.g. a stopcock or a stop valve, may be opened and the pump 405 may be operated in order to empty the effluent bag 400' into the basin 600 via the effluent outlet line 403.

Particularly, if the pump 405 is (but is not limited to) an impeller pump, which is not self-priming, it may be an advantage, if the effluent outlet line 403 is positioned inclining upwards towards basin 600. Alternatively or optionally, the effluent outlet line 403 runs sloping downwards between shut-off element 408 and pump element 405, so that air bubbles rise and may be fed towards basin 600 or, alternatively, towards the effluent bag 400'.

By this method, with reference to the illustrations in FIG. 6, the user advantageously ensures, for reasons of electrical safety (i.e., keeping below the permissible limits of the patient leakage currents), that the pump 131 for the effluent is stopped before the shut-off element 408 is opened and the pump 405 is operated.

The pump 405 may be designed as a pump, which is shown in FIG. 4 with the reference numerals 141 and 405a. The pump, shown by the elements with the reference numerals 141/405a, may be designed as disclosed in the German patent application for the applicant of the present application, filed with the German Patent and Trademark Office on Sep. 29, 2017 having the file reference number DE 102017122804.7. The respective disclosure is hereby made to the subject-matter of the present application by way of reference. Nevertheless, another pump may also be used.

Optionally the discharge hose system, that is arranged downstream of the effluent bag 400', does not comprise a flow-divider. However, the discharge hose system may comprise a roller pump, such as pump 405. The roller pump optionally may be connected to specifically one supply line and to specifically one discharge line. So that, clearly, the pump cannot divide the incoming flow into several flows.

Optionally, the discharge hose system, that is arranged downstream of the effluent bag 400' and/or downstream of the pump 405, does not comprise a connector.

Optionally, the discharge hose system, that is arranged downstream of the effluent bag 400', and/or upstream of the pump 405, does not comprise an element connected to an electrical control device, e.g. in form of an electrically connected connector.

An advantage of this variant of the method is that a conventional effluent bag 400' may be used. Only the effluent outlet line 403 downstream of the effluent bag 400' with the pump 405 must be supplemented. Thereby, the effluent outlet line 403 may comprise several or all features of the line 415 shown in the embodiment in FIG. 4 (or the above description) in any combination, in particular, several or all features of the line section downstream of the connector 411 shown in FIG. 4. To avoid repetition, reference is made to the description in FIG. 4.

LIST OF REFERENCE NUMERALS 25 coupling site for heparin (optional)
29 venous blood chamber (optional)
31 ventilation device
100 blood treatment apparatus
101 blood pump
102 dialysate outlet line, effluent inlet line
104 dialysis liquid inlet line
111 pump for substitute
121 pump for dialysis liquid
131 pump for dialysate or effluent in effluent inlet line
132 Connector
141 pump drive for pump 405 downstream of the 3-way-tap 401

143 weighing hook
150 control or closed-loop control device
200 source of dialysis liquid
201 substitute source, optional
300 extracorporeal blood circuit
301 first line (arterial line section)
302 (first) hose clamp
303 blood filter or dialyzer
303a dialysis liquid chamber
303b blood chamber
303c semi-permeable membrane
305 second line (venous line section)
306 (second) hose clamp
400 effluent bag
400' effluent bag
400a effluent inlet- or -outlet opening; effluent opening
400'a effluent inlet opening
400'b effluent outlet opening
401 three-way-tap, switching device
401a connector
401b connector
401c connector
401d grip section
403 effluent outlet line
405 pump in effluent outlet line
405a pump head
407 connection line
408 shut-off element, stopcock, stop valve
409 connector
411 connector
415 line
417 connector
419 non-return valve; check valve
421 fixing element or fastening device
423 end piece
600 basin
H2 bag heater with bag (dialysis liquid)
H1 bag heater with bag (substitute)
PS1, PS2 arterial pressure sensor (optional)
PS3 pressure sensor (optional)
PS4 pressure sensor for measuring the filtrate pressure

The invention claimed is:

1. A method of draining an effluent bag encompassing the steps:
providing an effluent bag to collect accumulated blood treatment effluent, the effluent bag comprising:
a closeable effluent opening or connection to an exterior of the effluent bag; and
operating a switching device of a discharge hose system connected to the effluent bag such that a fluid connection between an interior of the effluent bag and an interior of a connected effluent outlet line is established.

2. The method according to claim 1, wherein a pump drive is manually connected to a pump head fluidly coupled to the effluent outlet line.

3. The method according to claim 2, wherein a blood treatment apparatus comprises the pump drive.

4. The method according to claim 2, wherein an operation of the pump drive is manually started or stopped.

5. The method according to claim 1 further comprising:
operating the switching device such that a fluid connection between the interior of the effluent bag and the interior of the effluent outlet line is interrupted.

6. A blood treatment apparatus, connected to an effluent inlet line and to an effluent bag for collecting accumulated blood treatment effluent via the effluent inlet line, wherein:
the effluent bag is provided by a user of the blood treatment apparatus and comprises a closeable effluent opening or connection to an exterior of the effluent bag; and
the blood treatment apparatus comprises a control device, configured to carry out a method, the method comprising:
operating a switching device of a discharge hose system connected to the effluent bag such that a fluid connection between an interior of the effluent bag and an interior of a connected effluent outlet line is established.

7. The blood treatment apparatus according to claim 6, wherein the blood treatment apparatus is a hemodialysis apparatus, a hemofiltration apparatus, or a hemodiafiltration apparatus.

8. The blood treatment apparatus according to claim 6, wherein the blood treatment apparatus is an apparatus for chronic renal replacement therapy or an apparatus for continuous renal replacement therapy.

9. The blood treatment apparatus according to claim 6, further comprising:
a charging point for a voltage source for a pump drive of a pump, wherein a pump head of the pump is fluidly coupled to the effluent outlet line.

10. A discharge hose system comprising:
an effluent inlet line;
an effluent outlet line; and
a switching device, wherein the effluent inlet line and the effluent outline outlet line are each connected to the switching device,
wherein the switching device comprises a connector configured to establish a fluid connection between an effluent bag and the switching device, and
wherein the switching device is configured to fluidly connect (i) the connector and the effluent inlet line or (ii) the connector and the effluent outlet line.

11. The discharge hose system according to claim 10, further comprising an effluent bag to collect accumulated blood treatment effluent, the effluent bag comprising exactly one closeable effluent opening or connection to an exterior of the effluent bag.

12. The discharge hose system according to claim 10, further comprising a charging point for a voltage source for a pump drive of a pump, wherein a pump head of the pump is fluidly coupled to the effluent outlet line.

13. The discharge hose system according to claim 10, further comprising at least one connector pair connected to the effluent inlet line and the effluent outlet line.

14. The discharge hose system according to claim 10, wherein the switching device is or comprises at least one of a valve or a three-way-tap.

15. The discharge hose system according to claim 14, wherein the at least one of the valve or the three-way-tap comprises plastic or glass or the at least one of the valve or the three-way-tap is made of plastic or glass.

16. The discharge hose system according to claim 10, wherein the effluent outlet line is in conveying connection with at least one of at least one pump or a pump drive of a pump.

17. The discharge hose system according to claim 16, wherein the at least one of the at least one pump or the pump drive comprises:
a magnetically mounted and driven pump section; and
a pump head, wherein the pump head is an impeller pump head or a rotor.

18. The discharge hose system according to claim 16, wherein the at least one of the at least one pump or the pump drive comprises:
- a magnetically mounted pump section or a driven pump section; and
- a pump head, wherein the pump head is an impeller pump head or a rotor.

19. A method of draining an effluent bag of a blood treatment apparatus, the method comprising:
- providing an effluent bag defining an effluent inlet opening for effluent and an effluent outlet opening for effluent, the effluent inlet opening connected to an effluent inlet line via a connector, a first pump located along the effluent inlet line upstream of the connector, the effluent outlet opening connected to an effluent outlet line, a second pump located along the effluent outlet line, the effluent outlet line arranged to feed effluent into a basin;
- stopping the first pump for the effluent arranged along the effluent inlet line; and
- separating the effluent inlet line from the effluent inlet opening by disconnecting the connector.

20. The method according to claim 19, further comprising closing a shut-off element arranged along the effluent outlet line by shutting off a fluid flow via the shut-off element.

21. The method according to claim 20, wherein the shut-off element is only opened after the first pump arranged along the effluent inlet line has been stopped.

22. The method according to claim 21, further comprising:
- operating the second pump in order to empty the effluent bag into the basin via the effluent outlet line.

23. The method according to claim 19, further comprising:
- after separating the effluent inlet line from the effluent inlet opening, closing the effluent inlet line with a cap and/or closing the effluent inlet line using a manual hose clamp downstream of the first pump.

24. The method according to claim 19, wherein a portion of the effluent outlet line downstream of the effluent bag and/or upstream of the second pump does not comprise any element connected to an electrical control device.

\* \* \* \* \*